(12) United States Patent
Scholz et al.

(10) Patent No.: US 10,342,628 B2
(45) Date of Patent: Jul. 9, 2019

(54) INCISION PROTECTION

(71) Applicant: 3M INNOVATIVE PROPERTIES COMPANY, St. Paul, MN (US)

(72) Inventors: Matthew T. Scholz, Woodbury, MN (US); Nicholas R. Powley, St. Paul, MN (US); Ranjani V. Parthasarathy, Woodbury, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 848 days.

(21) Appl. No.: 14/428,663

(22) PCT Filed: Sep. 20, 2013

(86) PCT No.: PCT/US2013/060887
§ 371 (c)(1),
(2) Date: Mar. 17, 2015

(87) PCT Pub. No.: WO2014/047429
PCT Pub. Date: Mar. 27, 2014

(65) Prior Publication Data
US 2015/0245871 A1    Sep. 3, 2015

Related U.S. Application Data

(60) Provisional application No. 61/704,303, filed on Sep. 21, 2012.

(51) Int. Cl.
*A61B 46/00*    (2016.01)
*A61F 5/00*    (2006.01)
(Continued)

(52) U.S. Cl.
CPC .............. *A61B 46/00* (2016.02); *A61B 46/40* (2016.02); *A61F 5/00* (2013.01); *A61F 5/37* (2013.01);
(Continued)

(58) Field of Classification Search
CPC ... A61B 46/20; A61B 46/30; A61B 2046/205; A61B 17/02; A61B 46/00–40;
(Continued)

(56) References Cited

U.S. PATENT DOCUMENTS 1,810,466 A * 6/1931 Deutsch ................. A61B 17/02
128/850
3,060,932 A * 10/1962 Pereny ................... A61B 46/00
128/849

(Continued)

FOREIGN PATENT DOCUMENTS

CN       2612356      4/2004
CN     201082220      7/2008
(Continued)

OTHER PUBLICATIONS

Butson, M. J. et al.; "Lepton contamination and photon scatter produced by open field 18 MV X-ray beams in the build-up region"; Radiation Measurements; vol. 35; 2002; pp. 103-107.
(Continued)

*Primary Examiner* — Keri J Nelson
*Assistant Examiner* — Adam Baker
(74) *Attorney, Agent, or Firm* — 3M Innovative Properties Company; Jonathan V. Sry

(57) ABSTRACT

Surgical incise drapes including incision edge protectors are described. Methods of protecting the exposed edges of a surgical incision are also discussed.

17 Claims, 14 Drawing Sheets

(51) Int. Cl.
*A61F 5/37* (2006.01)
*A61B 17/08* (2006.01)
*A61B 46/20* (2016.01)

(52) U.S. Cl.
CPC ... *A61B 2017/086* (2013.01); *A61B 2046/205* (2016.02)

(58) Field of Classification Search
CPC .. A61B 2046/201–236; A61B 17/3209; A61B 17/32093; A61M 1/00
USPC ............... 128/850, 849, 853, 854, 855, 898
See application file for complete search history.

(56) References Cited

U.S. PATENT DOCUMENTS

| | | | |
|---|---|---|---|
| 3,236,370 A * | 2/1966 | Pereny | A61B 46/00 128/851 |
| 3,503,391 A | 3/1970 | Melges | |
| 3,522,800 A * | 8/1970 | Lesser | A61B 17/02 128/850 |
| 3,871,369 A | 3/1975 | Krzewinski | |
| 3,945,117 A * | 3/1976 | Beaver | A61B 17/32093 30/287 |
| 4,089,331 A * | 5/1978 | Hartigan | A61B 46/00 128/850 |
| 4,323,557 A | 4/1982 | Rosso et al. | |
| 4,598,004 A * | 7/1986 | Heinecke | A61F 13/023 428/131 |
| 4,689,338 A | 8/1987 | Gerster | |
| 4,701,509 A | 10/1987 | Sun et al. | |
| 4,732,808 A | 3/1988 | Krampe et al. | |
| 4,759,363 A * | 7/1988 | Jensen | A61B 17/32093 30/293 |
| 4,798,201 A | 1/1989 | Rawlings et al. | |
| 4,931,282 A | 6/1990 | Asmus et al. | |
| 5,017,625 A | 5/1991 | Ansell | |
| 5,069,907 A | 12/1991 | Mixon et al. | |
| 5,156,911 A | 10/1992 | Stewart | |
| 5,204,110 A | 4/1993 | Cartmell et al. | |
| 5,290,615 A | 3/1994 | Tushaus et al. | |
| 5,336,219 A * | 8/1994 | Krantz | A61B 17/085 606/213 |
| 5,443,488 A * | 8/1995 | Namenye | A61F 7/0097 165/46 |
| 5,750,134 A | 5/1998 | Scholz et al. | |
| 5,750,136 A | 5/1998 | Scholz et al. | |
| 6,000,106 A | 12/1999 | Kampfer et al. | |
| 6,132,660 A | 10/2000 | Kampfer | |
| 6,382,211 B1 * | 5/2002 | Crook | A61B 17/0293 128/849 |
| 6,484,371 B1 | 11/2002 | Romanko et al. | |
| 7,309,519 B2 | 12/2007 | Scholt et al. | |
| 7,683,234 B2 * | 3/2010 | Gurtner | A61L 15/42 523/111 |
| 7,727,547 B2 | 6/2010 | Fortune et al. | |
| 8,133,336 B2 | 3/2012 | Kettlewell et al. | |
| 8,135,504 B2 | 3/2012 | Kettlewell et al. | |
| 8,198,326 B2 | 6/2012 | Scholz | |
| 8,226,552 B2 | 7/2012 | Albrecht et al. | |
| 2001/0003986 A1 * | 6/2001 | Cosgrove | A61B 17/00234 128/898 |
| 2005/0034731 A1 * | 2/2005 | Rousseau | A61B 17/085 128/849 |
| 2005/0261631 A1 | 11/2005 | Clarke et al. | |
| 2008/0249526 A1 * | 10/2008 | Knowlton | A61B 17/32093 606/45 |
| 2010/0228182 A1 * | 9/2010 | Clark, III | A61B 18/1477 604/21 |
| 2011/0015557 A1 | 1/2011 | Aali et al. | |
| 2011/0183398 A1 | 7/2011 | Dasaratha et al. | |
| 2011/0197897 A1 * | 8/2011 | Touati | A61B 17/02 128/853 |
| 2011/0270301 A1 | 11/2011 | Cornet et al. | |
| 2014/0373851 A1 * | 12/2014 | Powley et al. | A61B 46/00 128/850 |

FOREIGN PATENT DOCUMENTS

| | | |
|---|---|---|
| WO | WO 2005/023233 | 3/2005 |
| WO | WO 2006/029255 | 3/2006 |
| WO | WO 2006/029278 | 3/2006 |
| WO | WO 2006/029351 | 3/2006 |
| WO | WO 2008-047059 | 4/2008 |
| WO | WO 2008047059 | 4/2008 |
| WO | WO 2011/022023 | 2/2011 |
| WO | WO 2011/022527 | 2/2011 |
| WO | WO 2011/128392 | 10/2011 |

OTHER PUBLICATIONS

De Boer, J.F. et al.; "Imaging thermally damaged tissue by polarization sensitive optical coherence tomography"; Optics Express; vol. 3, No. 6; 1998; pp. 212-218.

Lange-Asschenfeldt, B. et al.; "Distribution of Bacteria in the Epidermal Layers and Hair Follicles of the Human Skin"; Skin Pharmacology and Physiology; vol. 24; 2011; pp. 305-311.

Puhvel, S.M. et al.; "Quantification of Bacteria in Isolated Pilosebaceous Follicles in Normal Skin"; The Journal of Investigative Dermatology; vol. 65, No. 6; 1975; pp. 525-531.

* cited by examiner

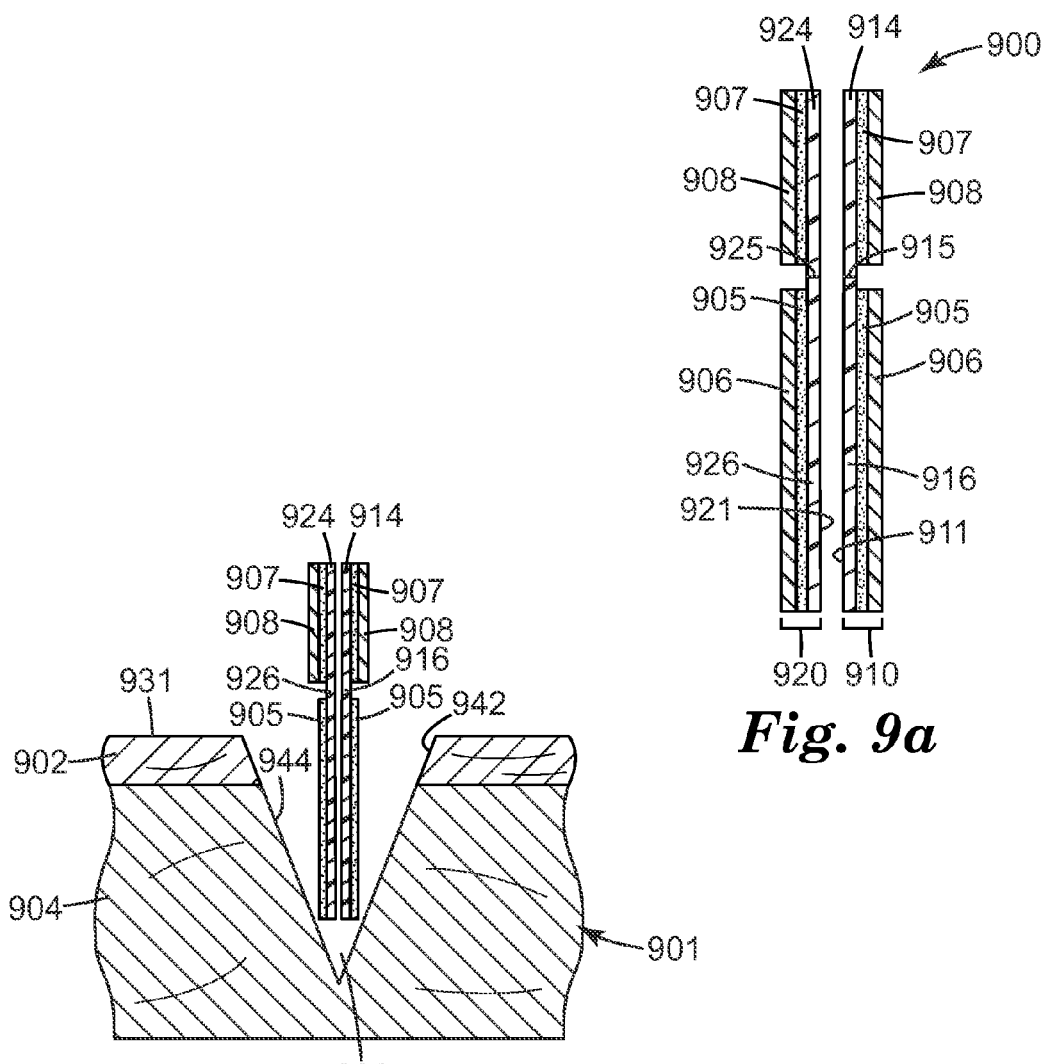
*Fig. 9a*
*Fig. 9b*
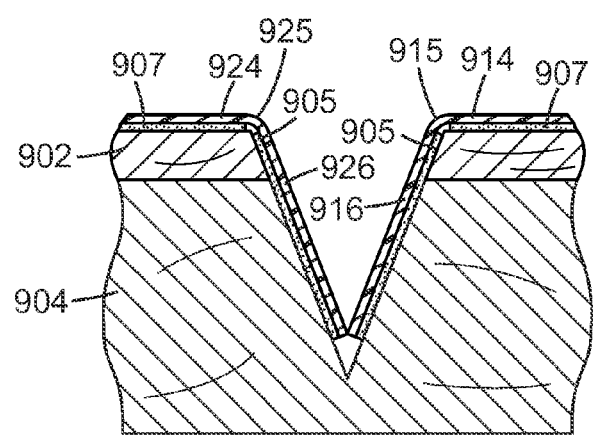
*Fig. 9c*

INCISION PROTECTION

CROSS REFERENCE TO RELATED APPLICATIONS

This application is a national stage filing under 35 U.S.C. 371 of PCT/US2013/060887, filed Sep. 20, 2013, which claims priority to U.S. Provisional Patent Application No. 61/704,303, filed Sep. 21, 2012, the disclosure of which is incorporated by reference in their entirety herein.

FIELD

The present disclosure relates to surgical incise drapes, specifically to incise drapes providing incision edge protection. Methods of using such incise drapes to protect an incision edge are also described.

SUMMARY

Briefly, in one aspect, the present disclosure provides a method of protecting an incision. The method includes forming a first incision in a skin comprising an epidermis extending from a surface to a first interface between the epidermis and a dermis, the dermis extending from the first interface to a second interface between the dermis and an adipose layer, wherein the adipose layer extends from the second interface to a third interface between the adipose layer and a subcutaneous layer; wherein the incision is bounded by two opposing cut edges of the skin having a first length and a first depth, wherein the first depth extends from the surface of the epidermis to a first distance greater than the first interface between the epidermis and the dermis thereby exposing an edge of the dermis; and covering the exposed edge of the dermis with a first barrier.

In some embodiments, the first distance is no greater than the third interface between the adipose layer and the subcutaneous layer. In some embodiments, the first distance is greater than the second interface between the dermis and the adipose layer. In some embodiments, the first distance is between 2 mm and 10 mm, inclusive.

In another aspect, the present disclosure provides a method of protecting an incision. The method includes forming a first incision in a skin comprising an epidermis extending from a surface to a first interface between the epidermis and a dermis, the dermis extending from the first interface to a second interface between the dermis and an adipose layer, wherein the adipose layer extends from the second interface to a third interface between the adipose layer and a subcutaneous layer; wherein the incision is bounded by two opposing cut edges of the skin having a first length and a first depth exposing an edge of the dermis, wherein the first depth extends from the surface of the epidermis to a first distance of at least 2 mm from the surface; and covering the exposed edge of the dermis with a first barrier.

In some embodiments, the method further includes forming a second incision in the skin having a second length and a second depth, wherein the second depth extends from the first distance to a second distance greater than the interface between the adipose layer and the subcutaneous layer after covering the exposed area of the dermis with the first barrier. In some embodiments, the second depth extends from the first distance to a second distance located at least 25 mm from the surface.

In some embodiments, covering the exposed area of the dermis with the first barrier comprises attaching the first barrier to at least a portion of the exposed area. In some the first barrier is adhered at least a portion of the exposed area with an adhesive. In some embodiments, the adhesive is a bioadhesive. In some embodiments, the adhesive further comprises an antimicrobial agent.

The above summary of the present disclosure is not intended to describe each embodiment of the present invention. The details of one or more embodiments of the invention are also set forth in the description below. Other features, objects, and advantages of the invention will be apparent from the description and from the claims.

BRIEF DESCRIPTION OF THE DRAWINGS

FIGS. 9a through 9c illustrate yet another exemplary incision edge protector and its method of use according some embodiments of the present disclosure.

DETAILED DESCRIPTION

A significant cause of surgical site infection (SSI) is believed to be contamination by the patient's own skin flora. In common surgical practice, the skin is decontaminated using antiseptic skin preps. Generally, these preps provide at least a 2 log reduction on a dry skin site such as the abdomen and at least a 3 log reduction on a wet skin site such as the groin. Despite the use of skin preps, viable bacteria may remain. For example, the groin may have an initial baseline bacterial count of 1,000,000 bacteria per square centimeter or more. Thus, even after using a prep that provides a 3 log reduction, 1000 bacteria per square centimeter may remain. As an additional infection prevention measure, a sterile adhesive coated film or incise drape may be adhered to the skin at the surgical incision site, creating a sterile top surface through which the incision is made incision directly through the incise drape.

Typically, forming an incision requires repeated incising steps as the incision is extended through the entire thickness of the skin, the underlying adipose layer, and other subcutaneous layers. During this process, gloved hands and sterilized instruments are inserted to spread the incision as the depth is increased. Ultimately, gloved hands and instruments are extended through the completed incision as well.

Generally, the use of preps prior to making an incision and the use of drapes while making the incision are directed toward preventing infections arising from surface bacteria. However, such methods do not address subsurface bacteria, i.e., bacteria present within the skin layer itself. The top 50 to 500 microns of incised skin is highly contaminated with bacteria that are not killed by the skin prep and not covered up by the incise drape. For example, it has been reported that a single hair follicle can contain over 35,000 bacteria. Other sources of subsurface bacteria include the sebaceous glands and sweat pores.

As gloved hands and surgical instruments are inserted into an incision, this subsurface bacterial may be spread deeper into the incision site. In addition, the use of fluid irrigation can spread these bacteria within and around the incision. A variety of products are available for protecting the edges of an incision. However, such products are inserted into the wound after the complete incision has been made. While such products protect the incision edge from being exposed to bacteria during the subsequent procedure, these products are not in place while the incision is being formed and would not prevent the spread of subsurface bacteria from the incision edge into subsurface layers by gloves, instruments, and irrigation prior to their insertion.

Figure 1:
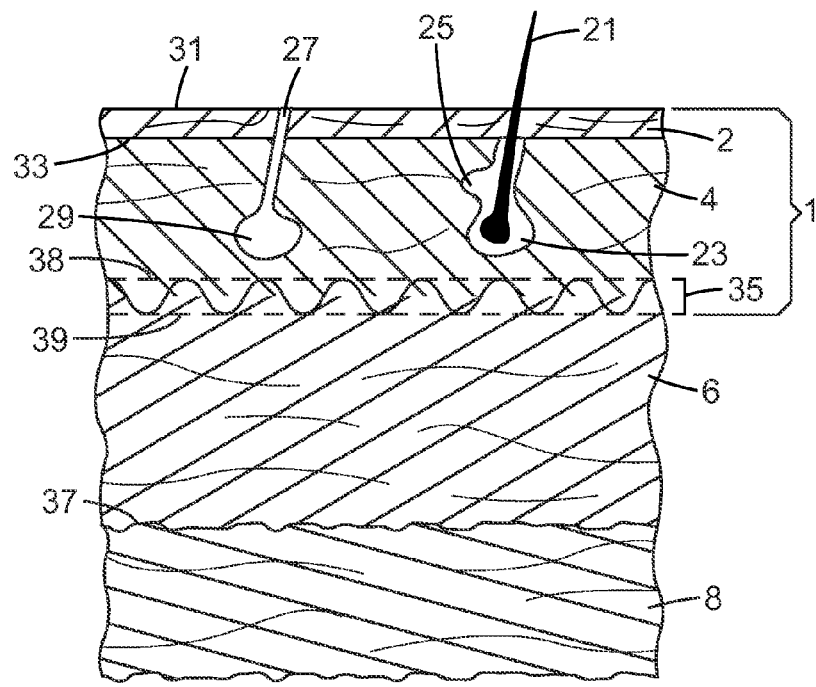
FIG. 1 illustrates a cross section of skin and underlying layers.

The present inventors have discovered methods and articles suitable for reducing or eliminating the spread of subsurface bacteria during and subsequent to incising. A cross section of skin 1 is illustrated in FIG. 1. Skin 1 has two layers: epidermis 2 is the outer layer and includes exposed surface 31, and dermis 4 is the inner layer extending from epidermis/dermis interface 33 to dermis/adipose interface 35. As shown, in general the boundary between the dermis and adipose layer undulates such that the distance from the exposed surface of the skin to this boundary varies. As used herein and as shown in FIG. 1, dermis/adipose interface 35 is a region with top surface 38 and bottom surface 39 substantially parallel to exposed surface 31, bounding this undulating boundary. Referring to FIG. 1, adipose layer 6 is shown extending from dermis/adipose interface 35 to adipose/interior interface 37, which separates adipose layer 6 from sub-adipose layers 8, which may include, e.g., muscle.

Figure 2:
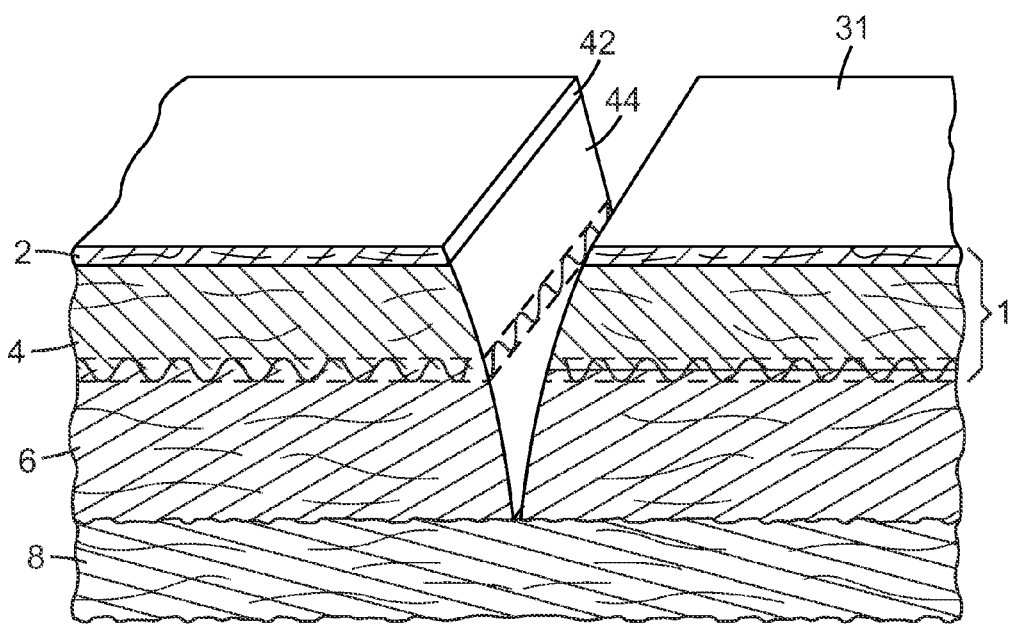
FIG. 2 illustrates the cross section of FIG. 1 after forming an incision.

Referring to FIG. 2, when an incision is formed through exposed surface 31 of skin 1, the edges of the various layers are exposed including, e.g., edge 42 of epidermis 2, edge 44 of dermis 4, and edge 46 of adipose layer 6. Although not shown, as the incision is extended deeper, edges of sub-adipose layers 8 would also be exposed.

As shown in FIG. 1, a variety of subsurface bacteria sources are present within dermis 4, including hair follicle 23, from which hair 21 extends; sebaceous gland 25, and sweat gland 29, from which sweat travels through sweat pore 27 to exposed surface 31. As an incision is made through dermis 4 bacteria from these sources can be released directly into the incision even with an incise drape in place. As the incision is extended into and beyond the adipose layer 6, these bacteria may be spread into sub-adipose layer(s) 8. Many of these bacteria such as *Staphylococcus aureus* (SA), a common cause of SSI, are known to go intracellular (i.e., inside mammalian cells) in less than sixty minutes where they are much less susceptible to antibacterial drugs and irrigation solutions. Thus, preventing the initial spread of these incision edge bacteria before the complete incision is formed is important.

Generally, an incision is formed by incising the skin with a sterile surgical instrument such as a scalpel. In prior methods, the complete incision is formed by making sequential incisions to extend progressively deeper into and through the skin, adipose, and sub-adipose layers.

Figure 3A:
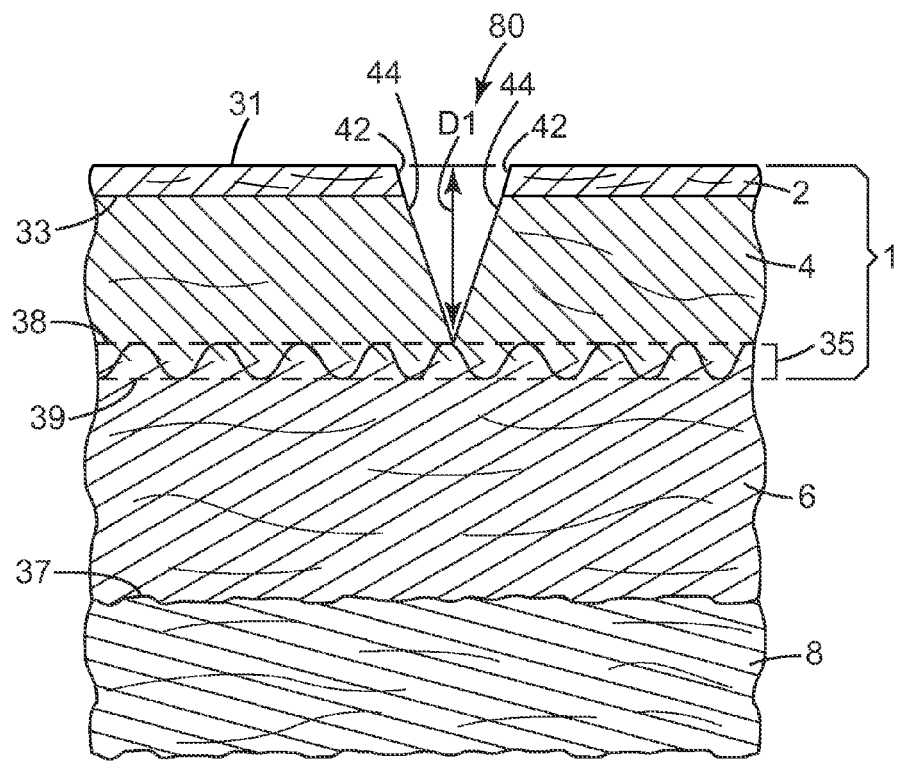
FIGS. 3a and 3b illustrate a method of covering an incision edge according to some embodiments of the present disclosure.

In an exemplary method of the present disclosure, an incision is formed in at least two discrete incising steps. In the first incising step, which comprises making one or more sequential incisions, the incision is extended from the exposed surface of the epidermis, into the dermis. Referring to FIG. 3a, in some embodiments, the depth D1 of incision 80 at the end of the first incision step extends from surface 31, through epidermis 2 and into dermis 4 to a position at least as deep as top surface 38 of dermis/adipose interface 35. In some embodiments, incision 80 extends into or even through dermis/adipose interface 35 and may extend into adipose layer 6. At the end of this first incising step, edges 42 of epidermis 2 and edges 44 of dermis 4 are exposed, and subsurface bacteria may have been released from, e.g. underlying skin cells, severed hair follicles, sebaceous glands, and sweat pores.

Prior to the second incising step, at least the edges of epidermis 2 and dermis 4 exposed during the first incising step are covered, inhibiting the spread of subsurface bacteria during the second incising steps and subsequent procedures. In some embodiments, a new, sterile surgical instrument may be used to continue the incision, replacing the tool used to make the first incision, which may be contaminated with subsurface bacteria.

Figure 3B:
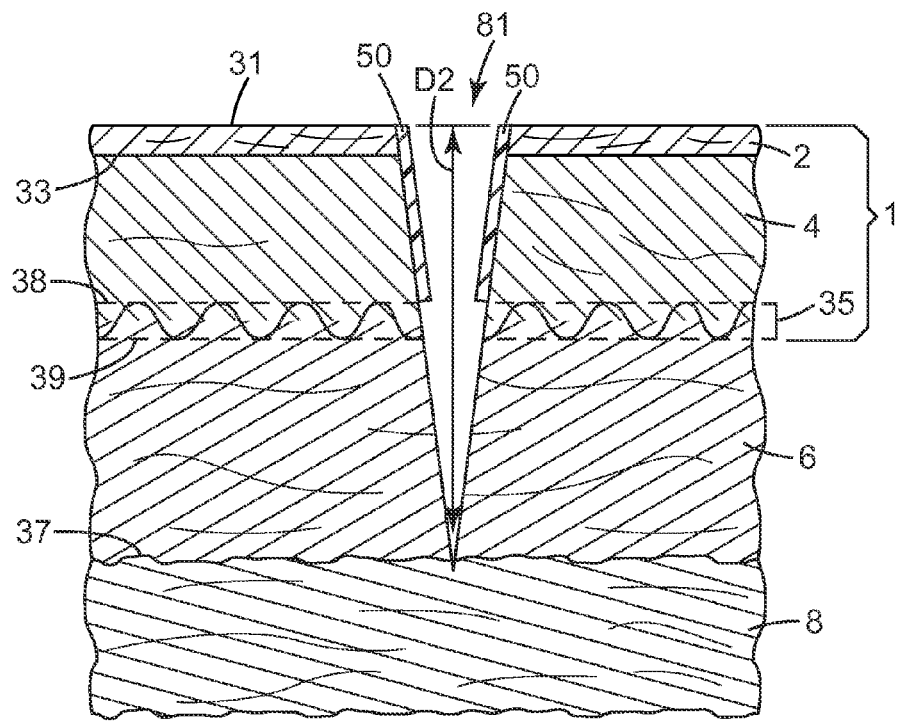

Referring to FIG. 3b, after covering the edges epidermis 2 and dermis 4 exposed by the first incising step with flaps 50, a second incising step is performed. The second incising step, which comprises making one or more sequential incisions, extends the depth of incision 80 from depth D1 to create incision 81 having depth D2, which is greater than depth D1. Depending on the location of depth D1, depth D2 may extend from surface 31 to a position below lower surface 39 of the dermis/adipose interface to a position within adipose layer 6, to adipose/sub-adipose interface 37, or even deeper. For example, in the exemplary embodiment of FIG. 3b, depth D2 extends into the sub-adipose layers 8. In some embodiments, depth D2 may extend to the desired location within the body, depending on the procedure being performed. For example, in some embodiments, depth D2 may extend into the abdominal cavity, or to the surface of a bone.

An exemplary incision edge protector ("IEP") and its use according to some embodiments of the present disclosure are illustrated in FIGS. 4a-4f. IEP 100 is positioned on surface 31 of the skin. In some embodiments, surface 31 has been treated with a prep. In some embodiments, surface 31 has been covered with, e.g., a drape. In such embodiments, IEP 100 would be located on the prepped skin or on the surface of the drape but, as used herein, would still be referred to as "positioned on the skin." Regardless of the surface IEP 100 is positioned upon, IEP 100 may be attached to that surface using any known attachment mechanism 105, e.g., an adhesive or mechanical attachment mechanism.

IEP 100 may be applied prior to or after the first incising step. However, IEP 100 is applied prior to the second incising step, i.e., before the full incision is completed. That is, IEP 100 may be applied prior to or after incising the skin from surface 31 to a first depth to create incision 180, but IEP 100 is applied prior to extending incision 180 in the second incising step.

Figure 4A:
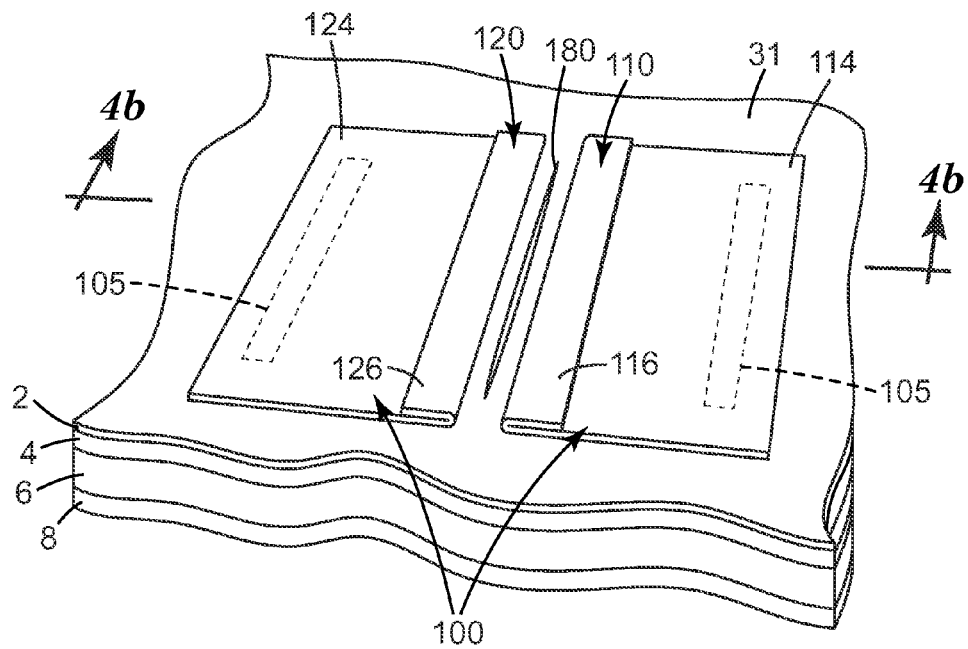
FIGS. 4a through 4f illustrate an exemplary incision edge protector and its method of use according some embodiments of the present disclosure.
Figure 4B:
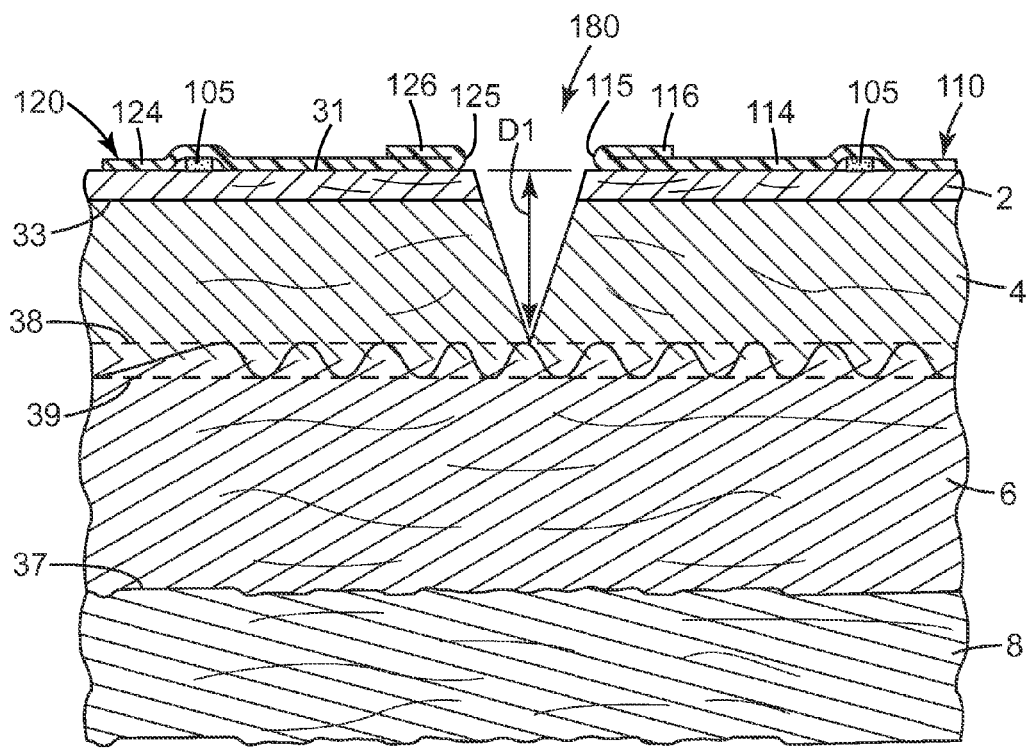
Figure 4C:
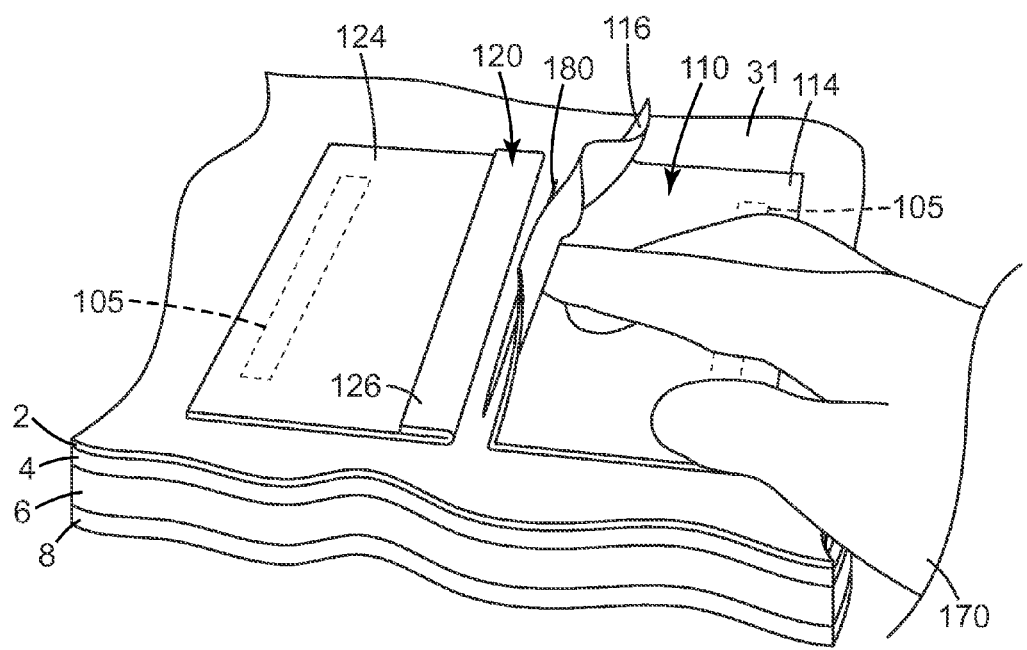

As illustrated in FIGS. 4a-4e, exemplary IEP 100 includes two portions 110 and 120 positioned on opposite sides of incision 180. Although first portion 110 and second portion 120 are shown as two discrete portions, in some embodiments, the two portions may be part of a single integrated article. Referring to FIGS. 4b and 4c, first portion 110 comprises a continuous layer, which includes first base 114 and first flap 116 separated by first fold 115. Similarly, second portion 120 includes second flap 126, separated from second base 124 by second fold 125. First base 114 and second base 124 are positioned on, and may be attached to, exposed surface 31 of the skin or alternatively, on an intermediate substrate such as a drape. For example, attachment mechanism 105 may be used to adhere first base 114 and second base 124 to exposed surface 31.

Suitable adhesives include acrylic adhesives, block copolymer adhesives such as those available under the trade name KRATON from Shell Chemical Company, Houston, Tex.), rubber based adhesives such as those based on natural rubber, polyisobutylene, butylene rubbers and the like, polyurethane type adhesives, and polyvinylethyl ether and copolymers or blends thereof. In some embodiments, the adhesive may be one of those described in U.S. Pat. Nos. 4,323,557; 4,931,282; 4,701,509; 4,732,808; 5,156,911; 5,017,625; and 5,204,110.

In some embodiments, the adhesive also contains an antimicrobial such as iodine, triiodide complexes, lactam-triiodide complexes such as povidone-iodine, chlorhexidine salts such as chlorhexidine gluconate and chlorhexidine acetate, polymeric biguanides, hexachlorophene, parachlorometaxylenol (PCMX), triclosan, phenols, fatty acid monoesters such as C8-C12 monoesters of propylene glycol and glycerin such as glycerol monolaurate, quaternary surfactants such as cetyltrimethyl ammonium chloride, silver, and silver salts such as silver chloride, silver oxide and silver, hydrogen peroxide and the like. These adhesive types may also include various chemical modifiers, e.g., tackifiers, crosslinkers, stabilizers, initiators, etc. to improve physical properties such as stability, viscosity, adhesion and the like.

Further, the adhesive may be a continuous coating or may be a pattern coated as described in U.S. Pat. Nos. 4,798,201 and 5,290,615. For example, in some embodiments, the entire base portions may be covered with adhesive to provide resistance to lifting of the base from the underlying skin during the incising and subsequent surgical steps. In some embodiments, the adhesive may be applied to discrete regions. For example, in some embodiments, it may be desirable to apply adhesive near the edge of the base near the incision site to inhibit lifting. In some embodiments, it may be desirable to provide adhesive some distance from the incision site to permit greater flexibility in adjusting the flaps such that they are properly aligned to provide the desired coverage of the exposed edges of the incision.

Generally, a wide variety of materials may be used to from the base and/or flap including those known for use in surgical drapes, incise drapes, and the like. In some embodiments, the material includes a flexible film. In some embodiments, the material is formed from a transparent or translucent polymeric material. The material preferably allows for moisture evaporation through the film during prolonged surgeries. Suitable materials include polyolefins, such as low density polyethylene and particularly metallocene polyethylenes such as those available under the trade name ENGAGE from Dow Chemical Company, polyurethanes such as polyester or polyether polyurethanes (e.g., those available under the trade name ESTANE from B. F. Goodrich, Cleveland Ohio), polyesters such as polyether polyester (e.g., those available under the trade name HYTREL from Du Pont Co., Wilmington, Del.), and polyamides such as polyether polyamides (e.g., those available under the trade name PEBAX from ELF Atochem, North America, Inc., Philadelphia, Pa.). In some embodiments, the material is flexible, and in some embodiments, somewhat elastomeric, to improve conformability when applied to a patient. For these reasons, the preferred films for certain embodiments are polyurethanes, polyether polyesters, and polyether polyamides. In some embodiments, the material may be cushiony, e.g., a foam. In some embodiments, the material may be fluid-filled. The material will typically have a thickness of less than about 200 microns, e.g., between about 6 microns to about 130 microns, e.g., between about 13 microns and about 52 microns.

Figure 4D:
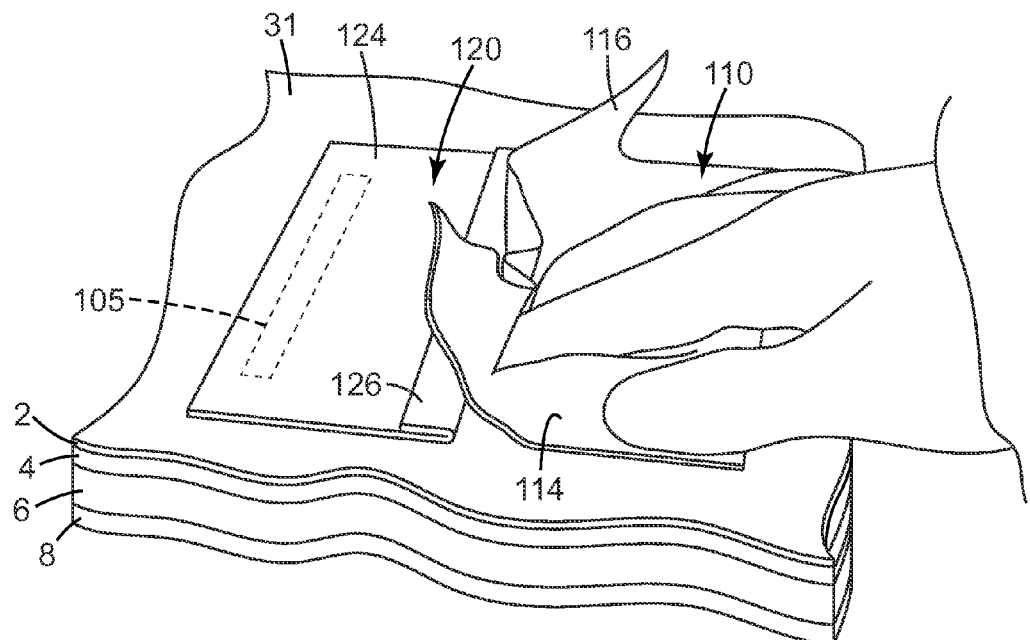
Figure 4E:
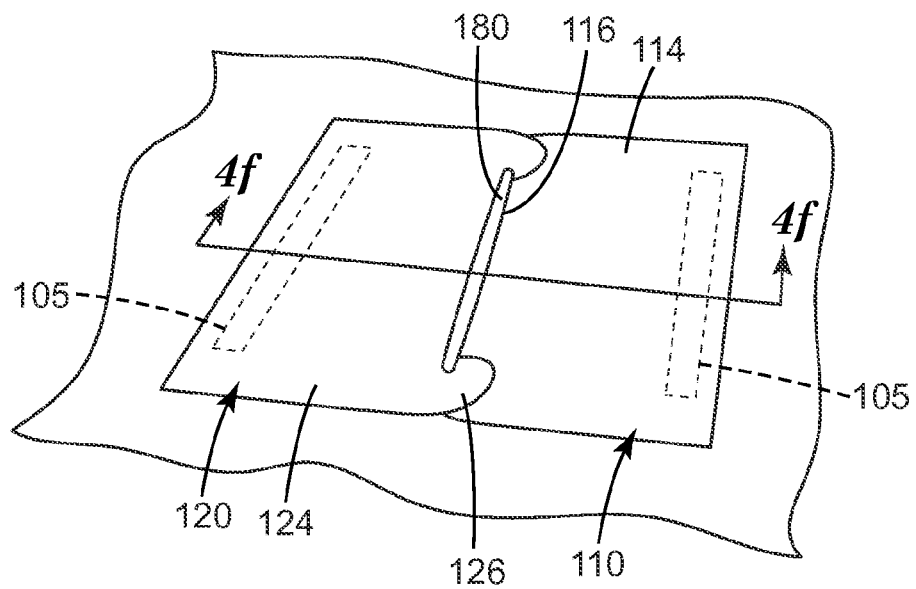

Referring to FIGS. 4c and 4d, after the first incising step, first portion 110 is unfolded and first flap 116 is inserted into incision 180. This process may be performed using, e.g., gloved hand 170 and/or an instrument. With respect to second portion 120, as shown in FIG. 4e, second flap 126 is similarly unfolded and inserted into incision 180.

Figure 4F:
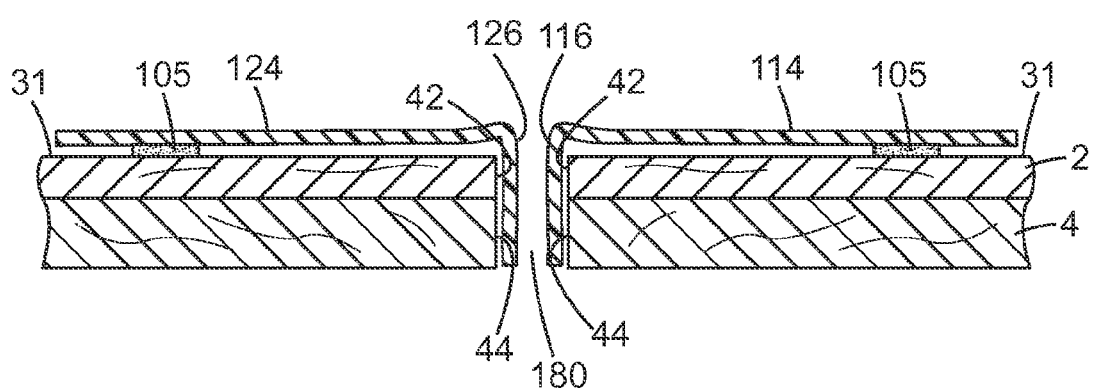

Referring to the cross section illustrated in FIG. 4f, first base 114 and second base 124 are attached via attachment mechanism 105 to exposed surface 31. First flap 116 and second flap 126 have been inserted into incision 180 covering exposed edges 42 of epidermis 2 and exposed edges 44 of dermis 4. Although it may be desirable to cover the entire exposed edge 44, due in part to the variability in depth that occurs when any incision is formed, and the difficulty that may arise in precisely positioning the flaps, complete coverage of exposed edge 44 may be impossible to achieve. Recognizing these limitations, in some embodiments, the flaps cover substantially all of exposed edge 44. For example, in some embodiments, the flaps cover an average of at least 90% of exposed edge 44 of dermis 4, and in some embodiments, at least 95% of exposed edge 44 of dermis 4. In some embodiments, it may be desirable to ensure that entire exposed edge of dermis is covered. In such embodiments it may be desirable to make the depth of the first incision such that it extends into the dermis/adipose interface. This will provide greater flexibility in aligning the flaps and covering the entire exposed edge of the dermis.

Figure 5A:
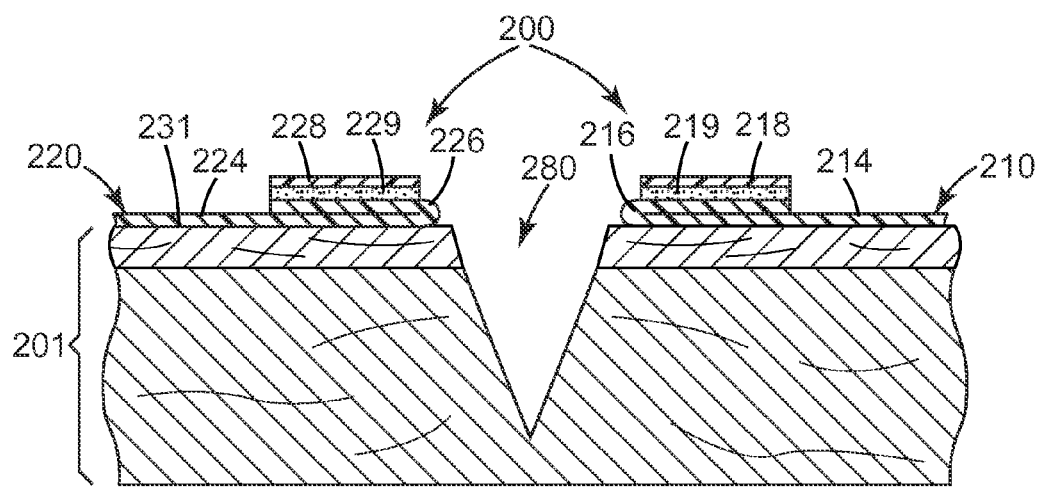
FIGS. 5a and 5b illustrate another exemplary incision edge protector and its method of use according some embodiments of the present disclosure.
Figure 5B:
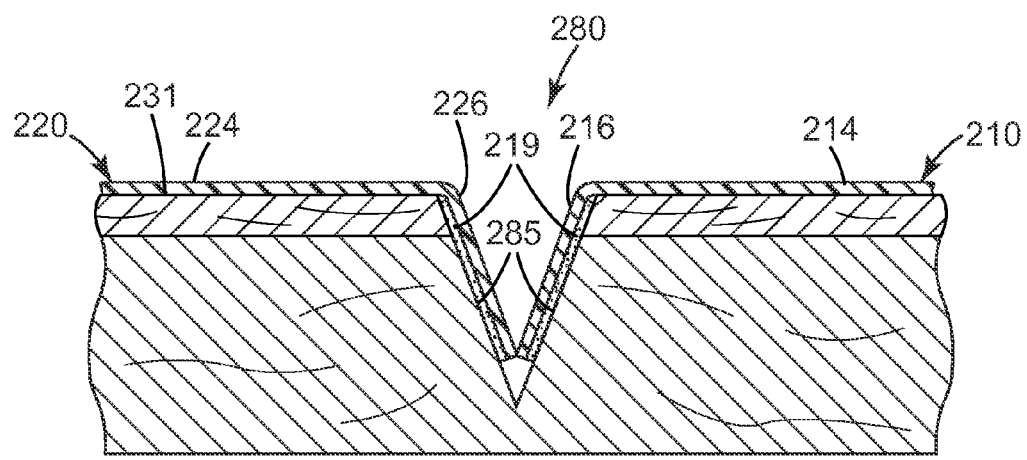

In some embodiments, it may be desirable to adhere or otherwise attach the flaps to at least a portion the exposed incision edge. An exemplary embodiment is illustrated in FIGS. 5a and 5b. Portions 210 and 220 of IEP 200 are positioned on exposed surface 231 of skin 201 on opposing sides of incision 280. As with all embodiments of the present disclosure, in some embodiments, exposed surface 231 has been treated with a prep. In some embodiments, exposed surface 231 has been covered with, e.g., a drape. In such embodiments, IEP 200 would be positioned on the prepped skin or on the surface of the drape. Regardless of which surface it is positioned upon, IEP 200 may be attached to that surface using, e.g., an adhesive or mechanical attachment mechanism.

First portion 210 includes first base 214 and first flap 216. First adhesive 219 is bonded to first flap 216. In some embodiments, first portion also includes first protective liner 218 covering the surface of first adhesive 219 opposite first flap 216. Generally, such protective liners are well-known and may be selected to provide the desired performance properties including remaining adhered to the adhesive prior to use, and being readily removable from the adhesive during use. Exemplary protective liners include release coated substrates such as silicone- and fluorosilicone-coated papers and films.

Second portion 220 similarly includes second base 224, second flap 226, second adhesive 229 and second protective liner 228. Prior to or during insertion of flaps 216 and 226 into incision 280, protective liners 218 and 228 are removed exposing adhesives 219 and 229. As shown in FIG. 5b, when the flaps are inserted into the incision, adhesives 219 and 229 adhere to at least a portion of exposed incision edges 285.

Any of a wide variety of adhesives could be used. In some embodiments, the adhesives are bioadhesives such as those known to adhere well to moist tissue. Examples of suitable bioadhesives that adhere well to moist tissue include slightly crosslinked polyacrylic acid. This may be UV cured or compounded as a hydrocolloid such as those found in U.S. Pat. Nos. 5,750,134 and 5,750,136. The bioadhesive also may adhere due to viscoelastic forces due to a coating of higher MW water soluble polymers. Many of the adhesive systems used in denture creams may be suitable. Preferred polymers are starches and other biocompatible polymers that can be degraded in the mammalian tissue and are rapidly water swellable or dissolvable. Particularly preferred are cellulose derivative, alginate, pectin, polyacrylic acid, hyaluronic acid, polyvinyl alcohol, polyvinyl pyrrolidone, and crosslinked polyacrylic acids and acrylic acid copolymers such as polycarbophil or Carbopol. The bioadhesive may chemically react with the tissue such as those described in U.S. Pat. Nos. 7,727,547; 8,133,336 and 8,133,504.

In some embodiments, the adhesive is antimicrobial to kill bacteria at the wound edge. Suitable antimicrobials include those disclosed in U.S. Pat. No. 8,198,326 and International Publication Nos. WO 2006/029351; WO 2006/029255 and WO 2005/023233, as well as other known antimicrobials. The adhesive may contain other actives to accelerate wound healing, reduce inflammation, reduce bleeding and the like. Actives may include analgesic, a healing factor, a vitamin, a growth factor, a nutrient, nitric oxide and nitric oxide releasing compounds and systems, nitroglycerin, antiinflammatory drugs, both steroidal (e.g., hydrocortisone, prednisolone, triamcinolone) and nonsteroidal (e.g., naproxen, piroxicam); antibacterials (e.g., penicillins such as penicillin V, cephalosporins such as cephalexin, erythromycin, tetracycline, gentamycin, sulfathiazole, nitrofurantoin, and quinolones such as norfloxacin, flumequine, and ibafloxacin); antiprotazoals (e.g., metronidazole); antifungals (e.g., nystatin); vasodilators; enzyme inhibitors such as collagenase inhibitors, protease inhibitors, elastase inhibitors, lipoxygenase inhibitors, antivirals and/or immunomodulators (e.g., 1-isobutyl-1H-imidazo[4,5-c]quinolin-4-amine, 1-(2-hydroxy-2-methylpropyl)-1H-imidazo[4,5-c]quinolin-4-amine, and other compounds disclosed in U.S. Pat. No. 4,689,338, incorporated herein by reference, acyclovir); local anesthetics (e.g., benzocaine, propofol); peptide hormones (e.g., human or animal growth hormones, LHRH); enzymes (e.g. papain, lysozyme, dextranase etc.); hemostatics and combinations thereof.

In some embodiments, a bioadhesive may be applied to the exposed incision edges and the flaps subsequently folded down and attached to the adhesive already in place. For example, a bioadhesive tape, strip, or hoop may be inserted after the first incision and adhered to at least a portion of the exposed incision edges. The flaps may then be inserted and attached to the adhesive.

Instead of or in conjunction with an adhesive, the flaps may be attached to the exposed incision edge with mechanical fasteners. For example, in some embodiments, the flaps comprise a texture which may be random or engineered that improves adhesion to the wound edge. In some embodiments the flaps comprise microreplicated needle or hook like structures that are designed to secure the flap to the newly created wound edge. For example, microneedles such as those disclosed in US2005/0261631 could be used. Stem structures such as those disclosed in U.S. Pat. No. 7,309,519 are also contemplated. Exemplary hook-type structures include those described in U.S. Pat. Nos. 6,000,106; 6,132,660; and 6,484,371 or other suitable hooks. These structures may be combined with the bioadhesives, antimicrobials, and/or other actives, including those disclosed herein.

Figure 6A:
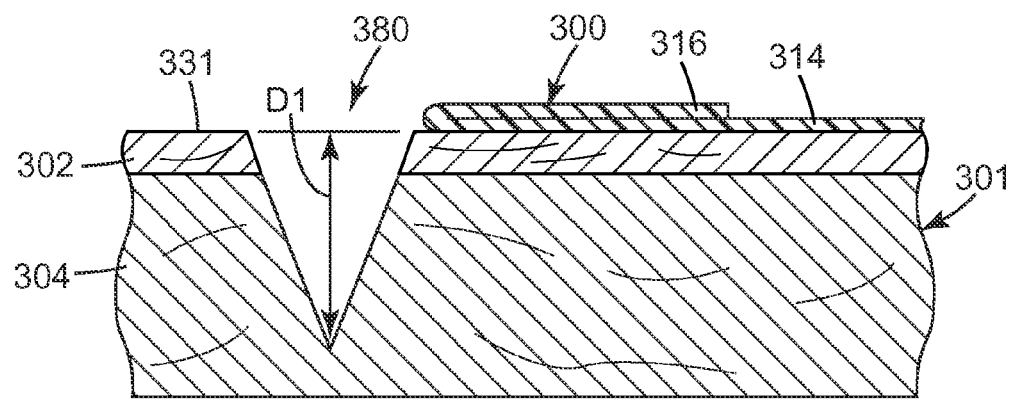
FIGS. 6a through 6c illustrate another exemplary incision edge protector and its method of use according some embodiments of the present disclosure.
Figure 6B:
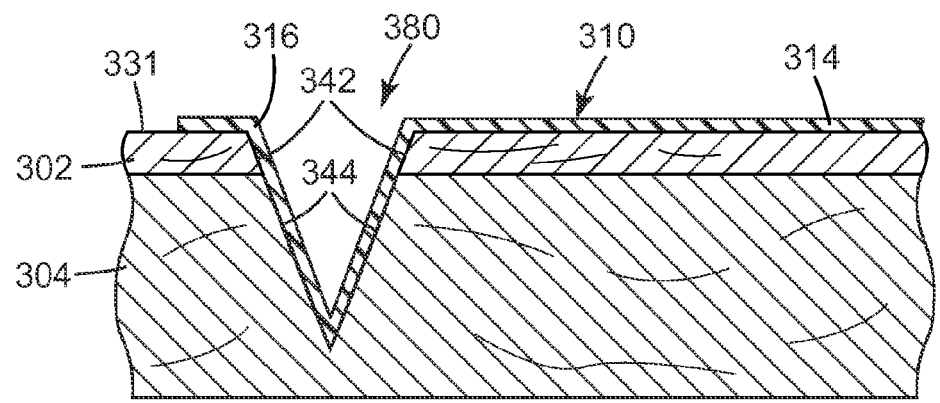
Figure 6C:
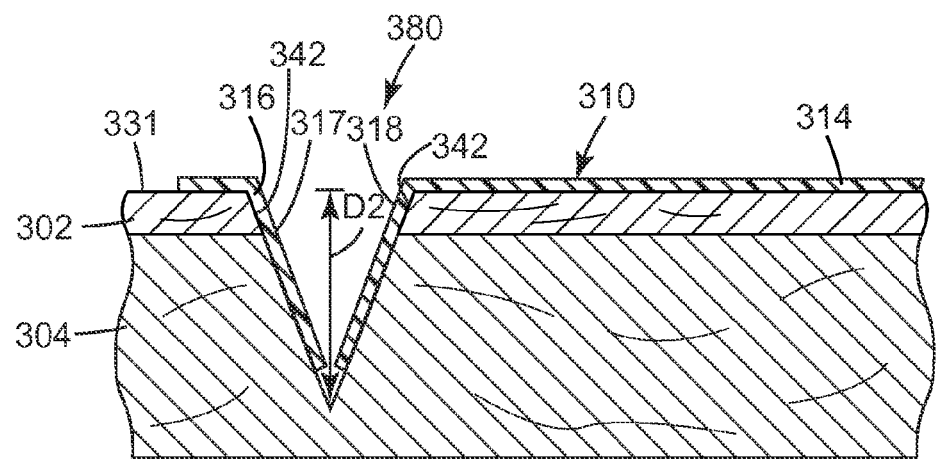

In another aspect of the present disclosure, the exposed incision edges can be covered using an IEP having a single portion. Referring to FIGS. 6a through 6c, IEP 300 is positioned on exposed surface 331 of skin 301 on one side of incision 380. IEP 300 may have positioned prior to or subsequent to the formation of incision 380. IEP 300 includes base 314, which may be adhered or otherwise attached to exposed surface 331, and flap 316.

Referring to FIG. 6b, after incision 380, which extends from exposed surface 331 to first depth D1, has been formed, flap 316 is folded over incision 380. A part of flap 316 is inserted into incision 380 to a sufficient depth to cover exposed areas 342 of epidermis 302 and exposed areas 344 of dermis 304. Referring to FIG. 6c, a second incise step is then performed, incising through flap 316 and extending incision 380 to second depth D2. As flap 316 is severed, first segment 317 and second segment 318 of flap 316 cover exposed areas 342 of epidermis 302 and exposed areas 344 of dermis 304. In some embodiments, an adhesive or other form of attachment may be located on at least a portion of flap 316, such that first segment 317 and second segment 318 can be attached to at least a portion of exposed areas 342 and/or 344.

Figure 7:
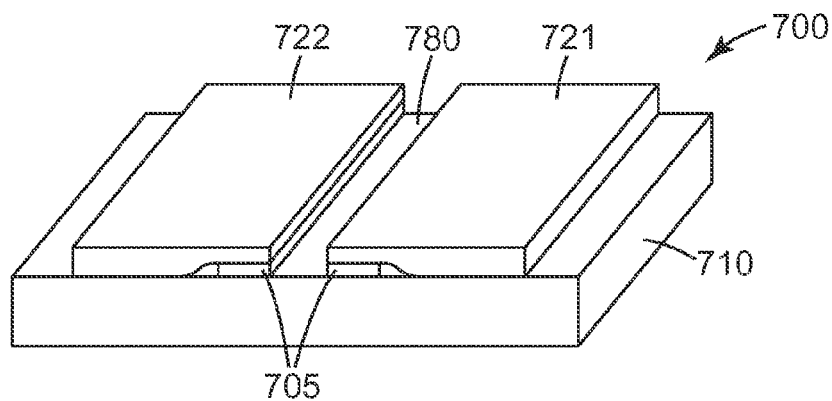
FIG. 7 illustrates another exemplary incision edge protector and its method of use according some embodiments of the present disclosure.

In some embodiments, it may be desirable to use a common base layer. Exemplary embodiments of such incision edge protectors are illustrated in FIG. 7. IEP 700 includes common base 710 and flaps 721 and 722. Flaps 721 and 722 are located on opposite side of incision zone 780 and are attached to base 710 by, e.g., adhesive 705. Although not required, generally, IEP 700 would be positioned prior to making the first incision, with incision zone 780 aligned with the desired location of the incision. In some embodiments, it may be desirable for base 710 to be translucent or transparent, at least in incision zone 780 such that IEP 700 may be properly aligned. After the incision has been made in incision zone 780 of base 710, flaps 721 and 722 may be folded over and inserted into the incision, protecting the exposed edges.

Figure 8A:
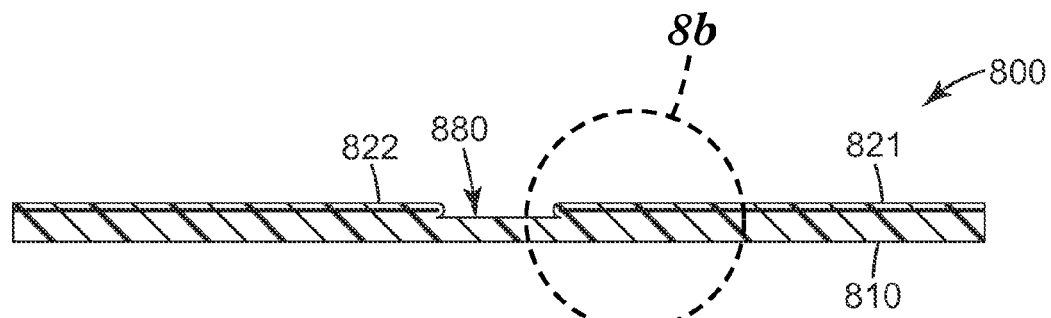
FIGS. 8a and 8b illustrate yet another exemplary incision edge protector and its method of use according some embodiments of the present disclosure.
Figure 8B:
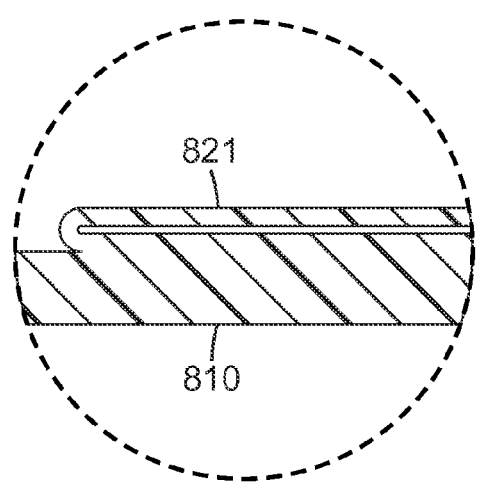

A similar embodiment is illustrated in FIGS. 8a and 8b. Here, IEP 800 is a unitary structure, with flaps 821 and 822 integral with and extending from common base 810. IEP 800 is aligned such that incision zone 880 is aligned with the desired incision location. This may occur before or after the initial incision is made. Then an incision is made through base 810 in incision zone 880. If IEP 800 is positioned on the skin prior to making the incision into the skin, the incision through base 810 may occur simultaneously with the formation of the incision into the skin to the desired initial depth. Next, flaps 821 and 822 may be folded over and inserted into the skin incision protecting the exposed areas of the epidermis and dermis.

In some embodiments, the common base made be formed from any suitable material, including those described previously for the base and/or flap materials. In some embodiments, the base may be a cushioning layer. For example, the base may comprise a foam, e.g. an open cell or closed cell foam. In some embodiments, the cushioning layer may be selected such that such that when it is adhered to the skin and incised through the incision zone, the retraction forces are dissipated to maintain circulation within the skin. Properties of the cushioning layer such as density, stiffness and/or thickness may be adjusted to provide the desired balance of properties.

In some embodiments, the base may include a fluid-filled region, particularly in the incision zone. When an incision is made through the incision zone, the fluid filled region will be opened, releasing the fluid into the incision. In some embodiments, the fluid may be suitable for flushing and/or irrigating the incision. In some embodiments, the fluid may comprise a therapeutic medicament. In some embodiments, the fluid may comprise an antimicrobial material. Generally, any known therapeutic medicament and/or antibacterial material may be used alone or in combination. Exemplary materials include iodine, triiodide complexes, lactam-triiodide complexes such as povidone-iodine, chlorhexidine salts such as chlorhexidine gluconate and chlorhexidine acetate, polymeric biguanides, hexachlorophene, parachlorometaxylenol (PCMX), triclosan, phenols, fatty acid monoesters such as Lauricidin (glycerol monolaurate), quaternary surfactants, silver, and silver salts such as silver chloride, silver oxide and silver, hydrogen peroxide and the like In some embodiments, it may be difficult to position an incision edge protector relative to an incision site such that the flaps extend to the desired depth within the incision. Even if the incision edge protector is positioned on the skin after the first incision is made, it may still be challenging to ensure the flap extends to the desired depth. In yet another aspect of the present disclosure, it may be useful to have an incision edge protector that is applied to the exposed edges prior to being attached to the exposed surface of the skin.

Referring to FIGS. 9a through 9c, one exemplary embodiment of such an incision edge protector and its use are illustrated. IEP 900 comprises first portion 910 and second portion 920. First portion 910 includes first substrate 911 comprising first base 914 and first flap 916 separated by first fold 915. Flap adhesive 905 is positioned between flap 916 and first liner 906. Base adhesive 907 is positioned between base 914 and second liner 908. Base adhesive 907 and flap adhesive 905 may be the same or different adhesives and may be selected from those adhesives described herein or other known adhesives. In some embodiments, mechanical attachment means such as microneedles may be used in conjunction with or in place of one or both adhesives.

Similarly, second portion 920 includes second substrate 921 comprising second base 924 and second flap 926 separated by second fold 925. Second portion also includes flap adhesive 905, base adhesive 907 and protective liners 906 and 908.

Referring to FIG. 9b, an incision 980 is formed in skin 901 extending from surface 931 to depth D1. Protective liners 906 are removed from flap adhesive 905 and flaps 916 and 926 are inserted into the incision. Flap adhesive 905 is used to adhere flaps 916 and 926 to the exposed incision edges 942 and 944. Referring to FIG. 9c, protective liners 908 are removed from base adhesive 907, bases 914 and 924 are folded along fold 915 and 925, respectively, and adhered to exposed surface 931 with base adhesive 907. In some embodiments, a single continuous adhesive layer may cover both the flap and the base of a particular portion, rather than the two discrete regions for each portion as shown in FIGS. 9a through 9c. Similarly, a single liner may be used for each portion, covering either two discrete adhesive regions or a single continuous region.

Figure 10A:
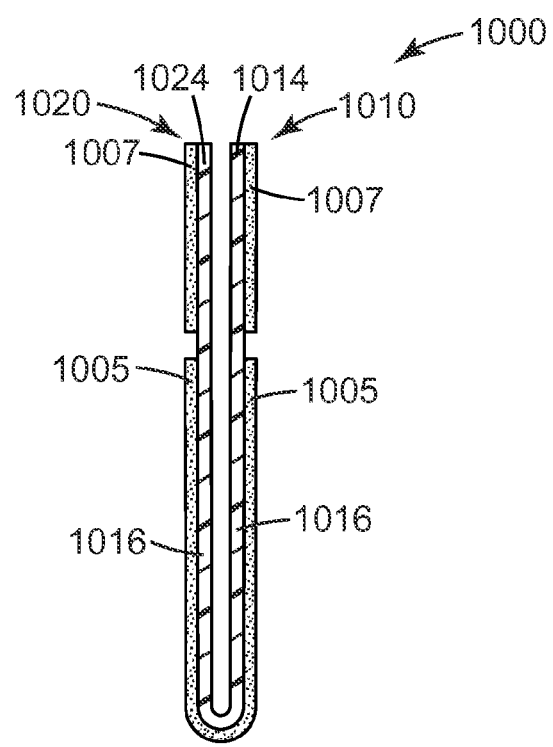
FIGS. 10a and 10b illustrate a further exemplary incision edge protector and its method of use according some embodiments of the present disclosure.
Figure 10B:
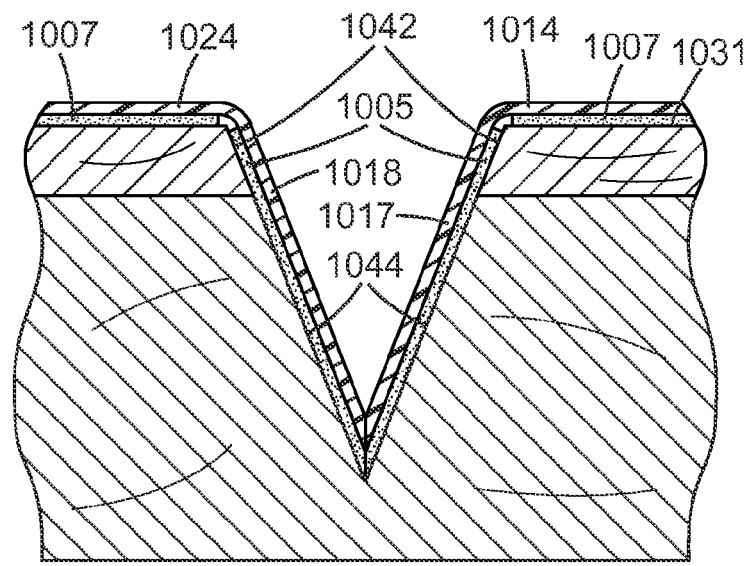

FIGS. 10a and 10b illustrate an alternative insertion incision edge protector according to some embodiments of the present disclosure. IEP 1000 is similar to IEP 900, except that flap 1016 extends continuously from first portion 1010 to second portion 1020. As shown in FIG. 10b, after insertion into an incision, flap 1016 would be severed, e.g., during the second incising step extending the depth of the incision, forming first segment 1017 and second segment 1018. These segments cover, and may be attached to exposed incision edges 1042 and 1044 using, e.g., flap adhesive 1005. Bases 1014 and 1024 are then folded, and adhered to surface 1031 with base adhesive 1007. Although not shown, protective liners may be used to cover one or both of flap adhesive 1005 and base adhesive 1007.

Figure 11A:
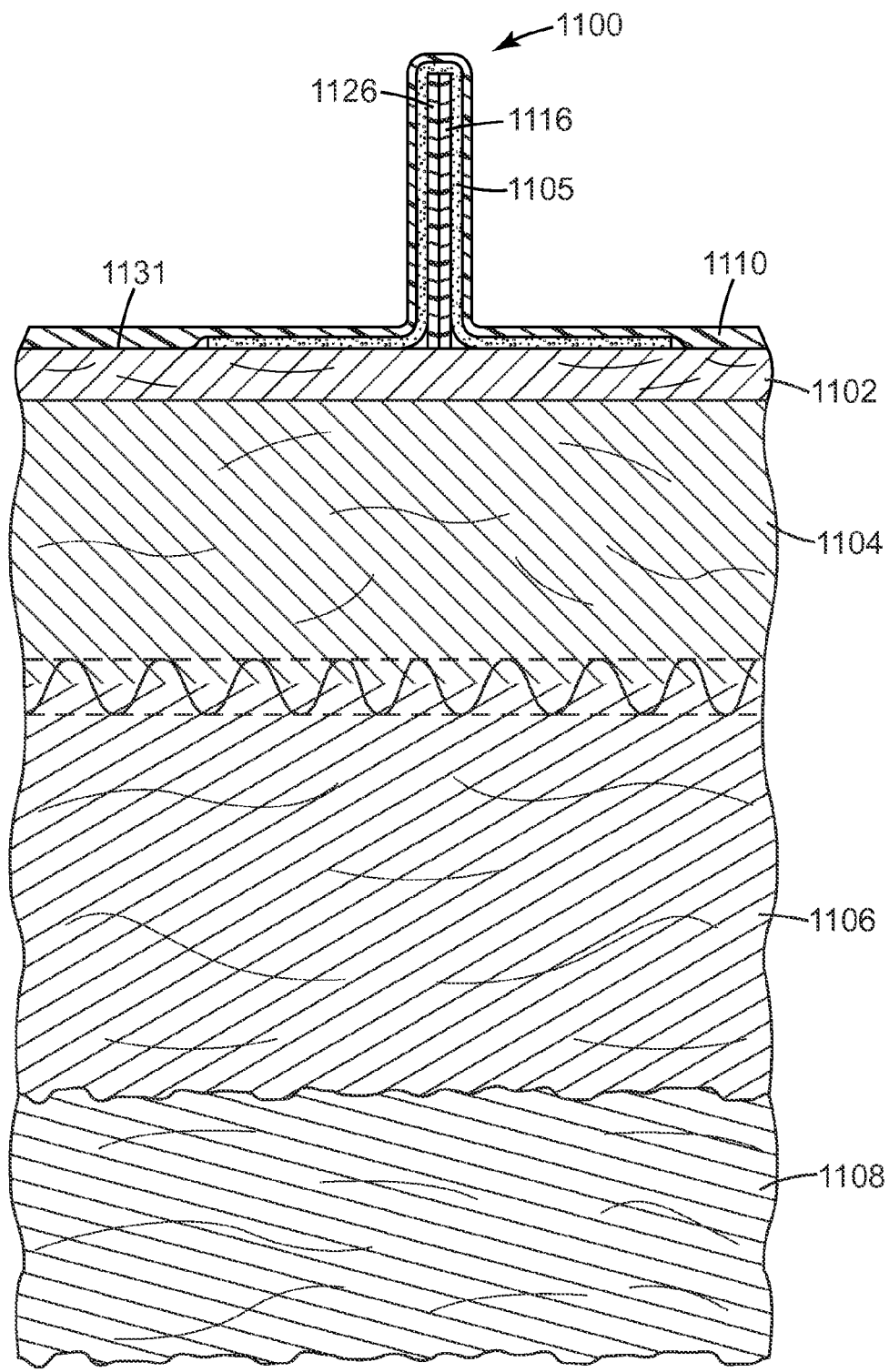
FIGS. 11a and 11b illustrate a further exemplary incision edge protector and its method of use according some embodiments of the present disclosure.
Figure 11B:
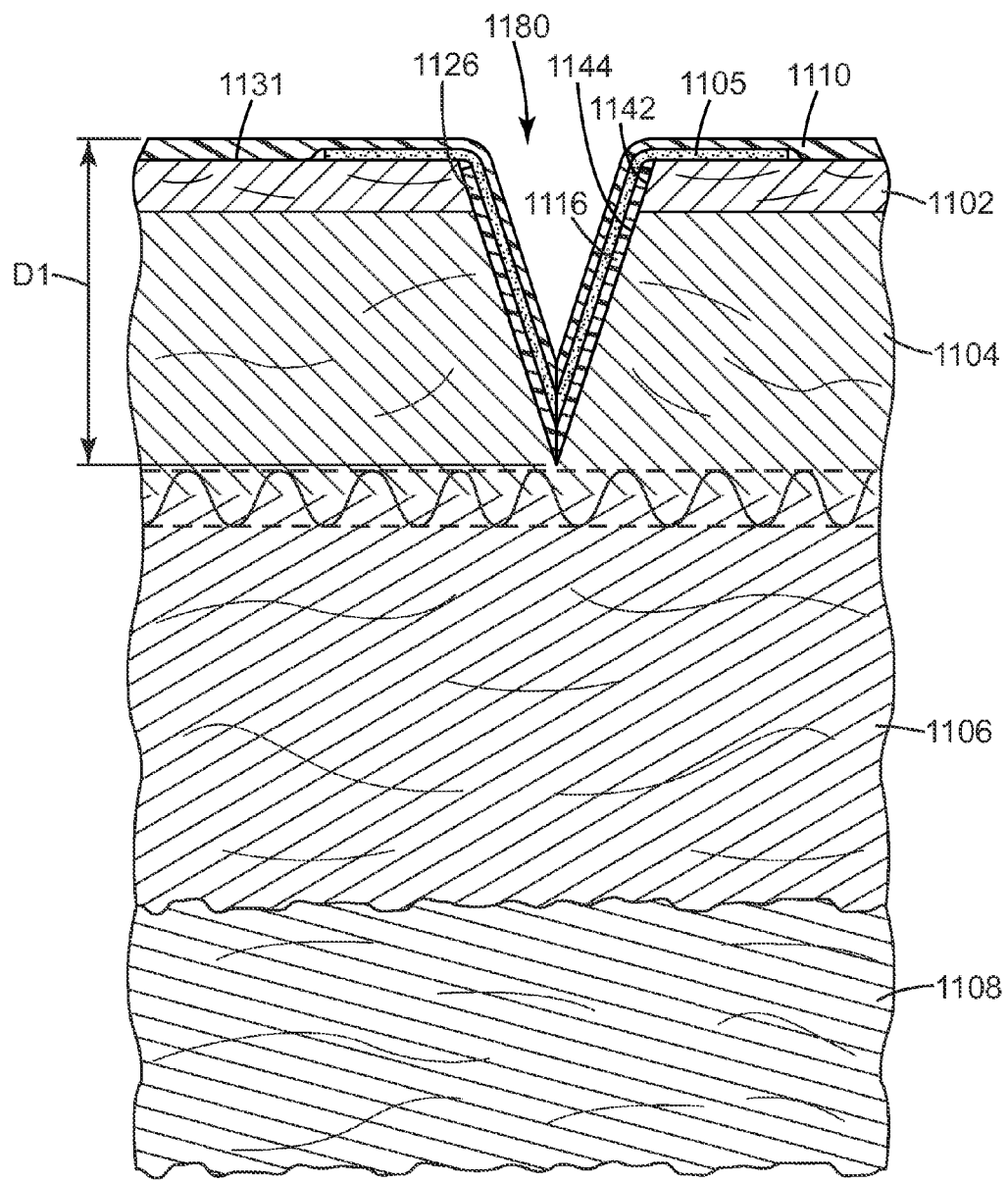

In some embodiments, it may be desirable to have self-inserting flaps. Exemplary self-inserting IEP 1100 and its use are shown in FIGS. 11a and 11b. IEP 1100 includes flaps 1116 and 1126, which may include optional attachment mechanisms such as adhesives and/or mechanical mechanisms to assist in the subsequent attachment of the flaps to the exposed edges of the incision. IEP 1100 also includes adhesive layer 1105 and base 1110. As shown in FIG. 11a, when positioned on surface 1131, flaps 1116 and 1126 are pressed up distorting base 1110. The material used to form base 1110 is selected to provide sufficient stiffness such that the distorted base generates a recovering force pressing the flaps back toward surface 1131.

As shown in FIG. 11b, when incision 1180 is formed, base 1110 and adhesive layer 1105 are severed. The recovery force presses flaps 1116 and 1126 into newly formed incision 1180 while or immediately after it is formed. Adhesive layer 1105 can then be used to adhere the flaps to exposed surfaces 1142 and 1144 of epidermis 1102 and dermis 1104, respectively, prior to a subsequent incising step extending the incision into adipose layer 1106 and sub-adipose layer 1108.

Various other embodiments of suitable incision edge protectors will be apparent to those skilled in the art based on the descriptions of the various incision edge protectors described in the present disclosure. Exemplary features that may be used alone or in combination with any one of the embodiments described herein are shown in FIG. 12.

Figure 12A:
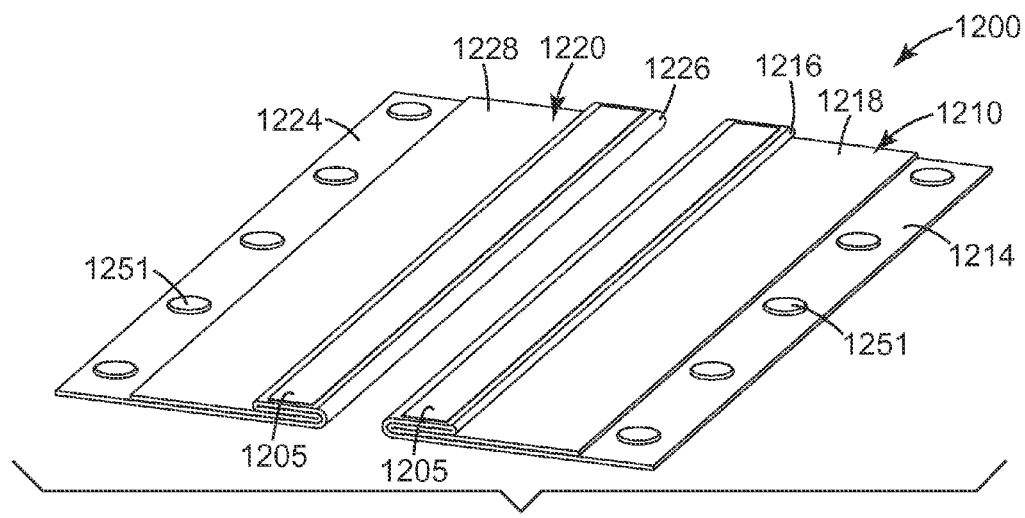
FIGS. 12a through 12g illustrate another exemplary incision edge protector and its method of use according some embodiments of the present disclosure.
Figure 12B:
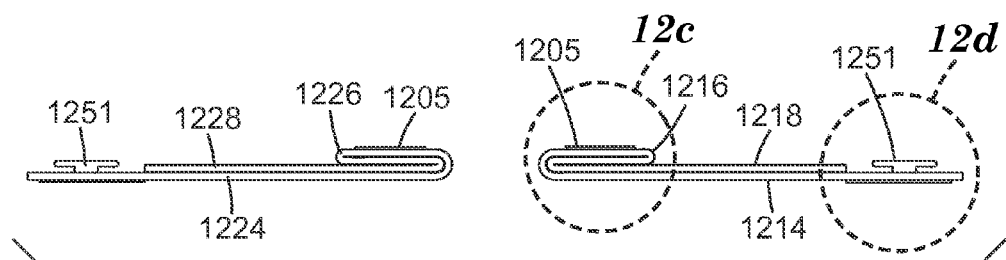

Referring to FIGS. 12a and 12b, IEP 1200 includes first portion 1210 and second portion 1220. First portion 1210 includes first base 1214, first flap 1216 and first wing 1218. Attachment mechanism 1205 is located on a portion of first flap 1216. Optionally, attachment mechanism 1205 may be covered by a protective substrate, e.g., a release liner (not shown). Similarly, second portion 1220 includes second base 1224, second flap 1226 and second wing 1228. Attachment mechanism 1205 is located on a portion of second flap 1226. Both first portion 1210 and second portion 1220 also include optional studs 1251, shown here aligned along an edge of bases 1214 and 1224, although other locations are also possible.

Figure 12C:
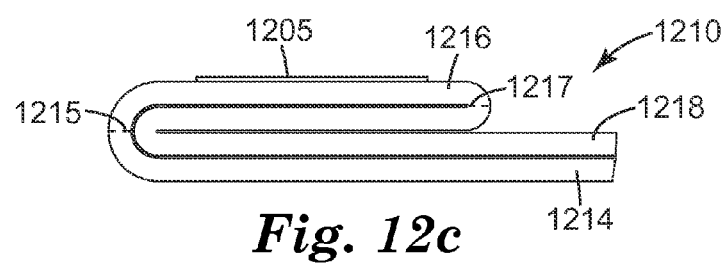

Referring to FIG. 12c, first portion 1210 is integrally formed. First flap 1216 extends from first base 1214 at first fold 1215. First wing 1218 extends from first flap 1216 at second fold 1217. Referring to FIGS. 12e and 12l, IEP 1200 is positioned on surface 1231 with first portion 1210 and second portion 1220 positioned on opposite sides of the incision site. First incision 1280 is formed, incising epidermis 1202 and dermis 1204. First flap 1216 and second flap 1226 are unfolded and inserted into incision 1280, with adhesive 1205 adhering the flaps to exposed area 1242 of epidermis 1202 and exposed area 1244 of dermis 1204.

Figure 12D:
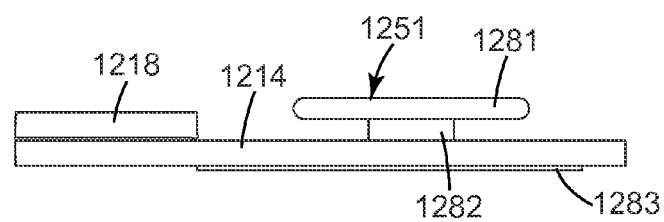
Figure 12E:
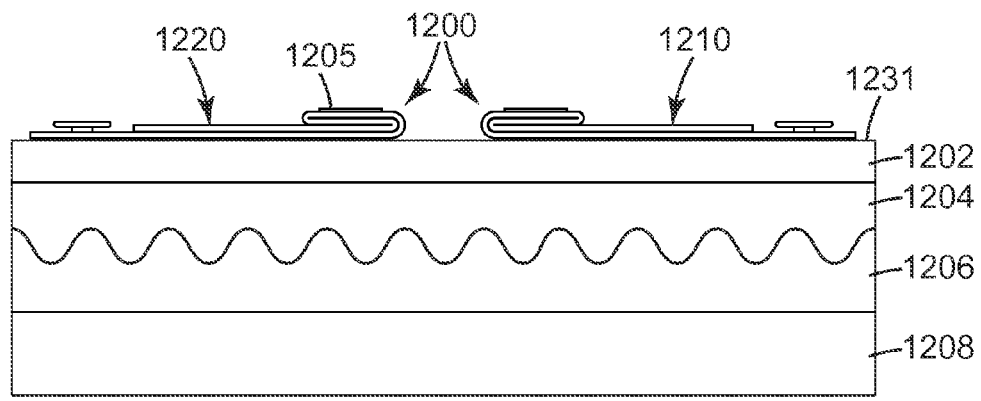
Figure 12F:
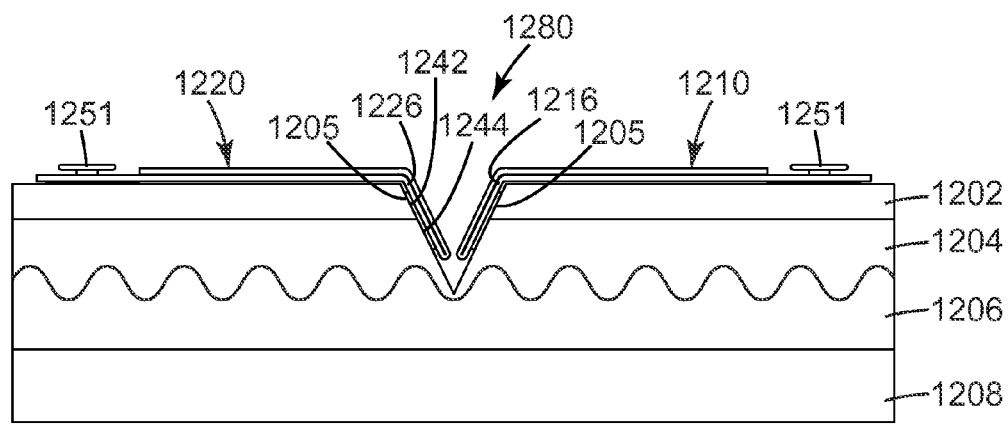
Figure 12G:
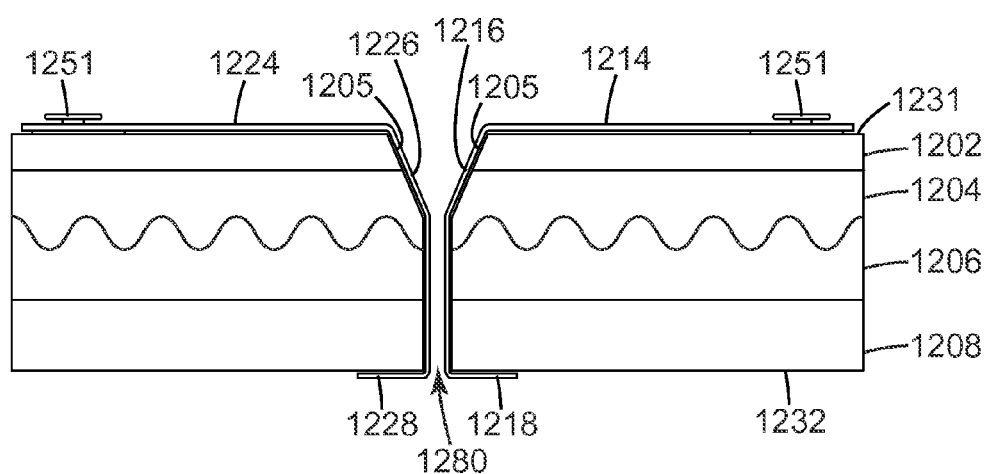

Referring to FIG. 12g, a second incision step is performed, extending incision 1280 through adipose layer 1206 and sub-adipose layers 1208, wherein lower surface 1232 bounds e.g., the abdominal cavity. First wing 1218 and second wing 1228 are then unfolded, inserted into incision 1280 and folded under sub-adipose layer 1208, while first base 1214 and second base 1224 remain on surface 1231.

Referring to FIGS. 12b and 12d, studs 1251 are shown inserted through bases 1214 and 1224. Head 1281 extend above the top surface of base 1214 from pin 1282. Pin 1282 extends from support 1283 which is attached, e.g., adhered to the lower surface of base 1214. Studs 1251 may be used for a variety of purposes such as attaching other drapes, warming blankets, and the like to the IEP. Studs 1251 may also provides support for fibers or strings to be strung from first portion 1210 to second portion 1220, across incision 1280. Such strings may be used to help close the incision following the procedure. In addition to or as an alternative to studs 1251, other mechanical attachment mechanisms may be used such as, e.g., snaps, hook and loop, rings, and the like. Also, adhesives may be used with or as an alternative to such mechanical attachment mechanisms.

Various modifications and alterations of this invention will become apparent to those skilled in the art without departing from the scope and spirit of this invention.

What is claimed is:

1. A method of protecting an incision comprising:
    forming a first incision in a skin comprising an epidermis extending from a surface to a first interface between the epidermis and a dermis, the dermis extending from the first interface to a second interface between the dermis and an adipose layer, wherein the adipose layer extends from the second interface to a third interface between the adipose layer and a sub-adipose layer; wherein the first incision is bounded by two opposing cut edges of the skin having a first length and a first depth, wherein the first depth extends from the surface of the epidermis to a first distance greater than the first interface between the epidermis and the dermis thereby exposing an edge of the dermis, wherein the first distance is no greater than the third interface between the adipose layer and the sub-adipose layer;
    covering the exposed edge of the dermis with a first barrier comprising a flexible film;
    forming a second incision in the skin having a second length and a second depth after covering an exposed area of the dermis with the first barrier, wherein the second depth extends from the first distance to a second distance greater than the third interface and the second incision extends further into the skin than the first barrier.

2. The method of claim 1, wherein the first distance is greater than the second interface between the dermis and the adipose layer.

3. The method according to claim 1, wherein the first distance is between 2 mm and 10 mm, inclusive.

4. The method according to claim 1, wherein the second depth extends from the first distance to a second distance located at least 25 mm from the surface.

5. The method according to claim 1, wherein covering an exposed area of the dermis with the first barrier comprises attaching the first barrier to at least a portion of the exposed area.

6. The method of claim 5, wherein the first barrier is adhered at least a portion of the exposed area with an adhesive.

7. The method of claim 6, wherein the adhesive is a bio adhesive.

8. The method according claim 7, wherein the adhesive further comprises an antimicrobial agent.

9. A method of protecting an incision comprising:
    forming, using a first instrument, a first incision in a skin comprising an epidermis extending from a surface to a first interface between the epidermis and a dermis, the dermis extending from the first interface to a second interface between the dermis and an adipose layer, wherein the adipose layer extends from the second interface to a third interface between the adipose layer and a sub-adipose layer; wherein the first incision is bounded by two opposing cut edges of the skin having a first length and a first depth exposing an edge of the dermis, wherein the first depth extends from the surface of the epidermis to a first distance of at least 2 mm from the surface, wherein the first distance is no greater than the third interface between the adipose layer and the sub-adipose layer; and
    covering the exposed edge of the dermis with a first barrier comprising a flexible film;
    forming a second incision in the skin having a second length and a second depth after covering the exposed area of the dermis with the first barrier, wherein the second depth extends from the first distance to a second distance greater than the third interface and the second incision extends further into the skin than the first barrier.

10. The method according to claim 9, wherein covering the exposed area of the dermis with the first barrier comprises attaching the first barrier to at least a portion of the exposed area.

11. The method of claim 10, wherein the first barrier is adhered at least a portion of the exposed area with an adhesive.

12. The method of claim 11, wherein the adhesive is a bio adhesive.

13. The method according claim 11, wherein the adhesive further comprises an antimicrobial agent.

14. The method of claim 9, wherein the second incision is formed using a second instrument.

15. The method of claim 9, wherein the first barrier comprises a first base attached to the skin and a first flap that forms a continuous layer with the first base.

16. The method of claim 15, wherein the first flap and the first base are covered with a single continuous adhesive layer.

17. The method of claim 9, further comprising treating the skin with a prep.

* * * * *

UNITED STATES PATENT AND TRADEMARK OFFICE
CERTIFICATE OF CORRECTION

Page 1 of 1

PATENT NO. : 10,342,628 B2
APPLICATION NO. : 14/428663
DATED : July 9, 2019
INVENTOR(S) : Matthew Scholz et al.

It is certified that error appears in the above-identified patent and that said Letters Patent is hereby corrected as shown below:

In the Specification

Column 9,
Line 27, after "like" insert -- . --.

Column 10,
Line 62, delete "121," and insert -- 12f, --, therefor.

In the Claims

Column 12,
Line 10 (Approx.), in Claim 8, after "according" insert -- to --.
Line 48 (Approx.), in Claim 13, after "according" insert -- to --.

Signed and Sealed this
Eleventh Day of February, 2020

Andrei Iancu
*Director of the United States Patent and Trademark Office*